United States Patent
Wada et al.

(10) Patent No.: US 12,251,396 B2
(45) Date of Patent: Mar. 18, 2025

(54) DIAGNOSTIC DRUG, DIAGNOSTIC METHOD AND DIAGNOSTIC DEVICE FOR PERMEABILITY OF INTESTINAL MUCOSA

(71) Applicants: National University Corporation Shimane University, Shimane (JP); KOYO CHEMICAL CO., LTD., Osaka (JP)

(72) Inventors: Koichiro Wada, Shimane (JP); Haruki Usuda, Shimane (JP); Morihiko Nakamura, Shimane (JP); Yoshimori Takamori, Tottori (JP); Seiji Kurozumi, Tottori (JP)

(73) Assignees: National University Corporation Shimane University, Shimane (JP); KOYO CHEMICAL CO., LTD., Osaka (JP)

( * ) Notice: Subject to any disclaimer, the term of this patent is extended or adjusted under 35 U.S.C. 154(b) by 26 days.

(21) Appl. No.: 18/131,192

(22) Filed: Apr. 5, 2023

(65) Prior Publication Data

US 2023/0233597 A1    Jul. 27, 2023

Related U.S. Application Data

(62) Division of application No. 16/478,421, filed as application No. PCT/JP2018/001266 on Jan. 17, 2018, now abandoned.

(30) Foreign Application Priority Data

Jan. 19, 2017  (JP) ................ 2017-007130

(51) Int. Cl.
*A61K 31/722*  (2006.01)
*A61K 9/00*    (2006.01)
*A61K 49/00*   (2006.01)

(52) U.S. Cl.
CPC .......... *A61K 31/722* (2013.01); *A61K 9/0031* (2013.01); *A61K 9/0053* (2013.01); *A61K 49/0004* (2013.01)

(58) Field of Classification Search
CPC . A61K 31/722; A61K 5/4255; A61B 5/14546
See application file for complete search history.

(56) References Cited

U.S. PATENT DOCUMENTS

2002/0022601 A1  2/2002  Konno et al.
2003/0068315 A1  4/2003  Wyss et al.
(Continued)

FOREIGN PATENT DOCUMENTS

JP  2002-332243 A   11/2002
JP  2014-503829 A    2/2014
(Continued)

OTHER PUBLICATIONS

Zeng et al., "Absorption and distribution of chitosan in mice after oral administration" Carbohydrate Polymers vol. 71 pp. 435-440, doi:10.1016/j.carbpol.2007.06.016 (Year: 2018).*
(Continued)

*Primary Examiner* — Eric Olson
(74) *Attorney, Agent, or Firm* — RANKIN, HILL & CLARK LLP

(57) ABSTRACT

Provided is a diagnostic drug for evaluating permeability of intestinal mucosa, including chitin and/or chitosan as a main component. The chitin and/or chitosan to be used preferably has a weight average molecular weight prepared to a range of from 1,000 to 11,600.

10 Claims, 20 Drawing Sheets

(56) References Cited

U.S. PATENT DOCUMENTS

| | | |
|---|---|---|
| 2005/0191289 A1 | 9/2005 | Wyss et al. |
| 2008/0075691 A1 | 3/2008 | Yamamoto et al. |
| 2012/0196299 A1 | 8/2012 | Vojdani |
| 2013/0309220 A1 | 11/2013 | Matalon |
| 2014/0186855 A1 | 7/2014 | Vojdani |
| 2014/0363673 A1 | 12/2014 | Minami et al. |
| 2015/0147277 A1 | 5/2015 | Dorshow et al. |

FOREIGN PATENT DOCUMENTS

| | | |
|---|---|---|
| JP | 2016151559 A | 8/2016 |
| WO | 2008/148503 A1 | 12/2008 |

OTHER PUBLICATIONS

International Search Report (ISR) dated Apr. 17, 2018 filed in PCT/JP2018/001266.

Gilani, S. et al., 'New biomarkers for increased intestinal permeability induced by dextran sodium sulphate and fasting in chickens, Journal of Animal Physiology and Animal Nutrition, Oct. 11, 2016, vol. 101, No. 5, pp. 237-245.; Cited in ISR.

Alonso, M. J., Sanchez, A., "Biodegradable Nanoparticles as New Transmucosal Drug Carriers", ACS Symposium Series 879 Carrier-Based Drug Delivery, 2004, pp. 283-295.; Cited in ISR.

Chae et al., "Influence of molecular weight on oral absorption of water soluble chitosans", Journal of Controlled Release, vol. 102 pp. 383-394, doi: 10.1016/j.jconrel .2004.10.012 (Year: 2005); Cited in USPTO Communication dated Aug. 1, 2022 and Dec. 9, 2022.

Guan et al., "Low Dosage of Chitosan Supplementation Improves Intestinal Permeability and Impairs Barrier Function in Mice", Bio Med Research International, vol. 2016, Article ID 4847296, 5 pages http://dx.doi.org/10.1155/2016/4847296 (Year: 2016); Cited in USPTO Communication dated Aug. 1, 2022 and Dec. 9, 2022.

Machova et al., "Ultrasonic depolymerization of the chitin-glucan complex from Aspergillus niger and antimutagenic activity of its product" Ultrasonics Sonochemistry, vol. 6, pp. 111-114 (Year: 1999); Cited in USPTO Communication dated Aug. 1, 2022 and Dec. 9, 2022.

* cited by examiner n=3, Mean+SD, *:p<0.05 RELATIVE TO CONTROL

**; $p<0.01$ RELATIVE TO EACH CONTROL n=3-7, Mean+SD
**; $p<0.01$ RELATIVE TO CONTROL
*; $p<0.05$ RELATIVE TO EACH CONTROL
†; $p<0.05$ FOR IR AT MOLECULAR WEIGHT OF 11,600 RELATIVE TO IR AT MOLECULAR WEIGHT OF 1,000

DIAGNOSTIC DRUG, DIAGNOSTIC METHOD AND DIAGNOSTIC DEVICE FOR PERMEABILITY OF INTESTINAL MUCOSA

TECHNICAL FIELD

The present invention relates to a technology for evaluating permeability of intestinal mucosa, and more particularly, to a technology for evaluating a degree of leaky gut syndrome and a technology for identifying or evaluating an inducer or inhibitor thereof.

BACKGROUND ART

There are various diseases based on permeability of intestinal mucosa, and for example, leaky gut syndrome (hereinafter referred to simply as "LGS" as appropriate) is known. LGS refers to a condition in which a food molecule, foreign matter, or the like penetrates into blood from the intestinal mucosa, and it is considered that this leads to occurrence of diarrhea or occurrence of allergic symptoms.

As a method of determining whether or not LGS is present, there is known a lactulose-mannitol test.

This method involves allowing a test subject to simultaneously take 10 g of lactulose (molecular weight≈340) and 5 g of mannitol (molecular weight≈180), and measuring a ratio between concentrations of lactulose and mannitol (L/M ratio) in urine, to thereby evaluate damage to an intestinal tract, i.e., a degree of leakage. The test utilizes the fact that, when the test subject is healthy, mannitol passes through the intestinal mucosa while lactulose hardly passes through the intestinal mucosa from the viewpoint of a molecular weight. A liquid chromatograph-mass spectrometer or the like is used for the measurement.

In addition, as an animal experiment, there is also known an FITC-dextran test.

This test involves orally administering FITC-dextran (fluorescence-labeled dextran) having an average molecular weight of about 4,000, and measuring its blood concentration. A fluorometer or the like is used for the measurement.

However, hitherto, the following problems have been known.

First, there has been a problem in that LGS does not have a sufficient definition that is definite, and a detection method or diagnostic method therefor has not been established. Conversely, this may be expressed as follows: because the detection method or diagnostic method has not been established, the definition is not definite.

In actuality, even in the lactulose-mannitol test, because urine is used, accurate measurement cannot be performed when a renal disorder is present. In addition, sugars, such as lactulose and mannitol, are absorbed through the intestinal mucosa by means of a special transporter, and hence there is also a possibility of a transport disorder due to the transporter itself.

In addition, there has also been a problem in that lactulose has a relatively small molecular weight, and hence it cannot be evaluated whether the test subject is in a state in which a substance having a larger molecular weight is also absorbed by an intestine (migrates to blood).

Meanwhile, the FITC-dextran has a somewhat large molecular weight, but has had a problem in that FITC has toxicity, preventing its use for a human.

Further, there are many reports that blood of an enteritis-affected individual or an individual who excessively ingests a high-fat diet contains a lipopolysaccharide having an average molecular weight of from 5,000 to 8,000. There has also been a problem in that a technology for evaluating leakiness of a substance having such large molecular weight does not exist in the first place.

That is, hitherto, there have been problems in that evaluation of the permeability of the intestinal mucosa typified by LGS is indirect, does not have high reliability, and has a narrow evaluation range.

CITATION LIST

Patent Literature

[PTL 1] JP 2016-151559 A

SUMMARY OF INVENTION

Technical Problem

The present invention has been made in view of the foregoing, and an object of the present invention is to provide a technology capable of directly evaluating the degree of permeability of intestinal mucosa with high reliability. As an example, the object is to provide a technology for diagnosing an increase in intestinal mucosal permeability, such as LGS.

Another object of the present invention is to provide a technology for determining a food and drink that affects permeability of intestinal mucosa. As an example, the object is to provide a technology for determining a food and drink that induces LGS or a food and drink that inhibits LGS.

Still another object of the present invention is to provide a technology for giving an objective evaluation of a pharmaceutical for normalizing permeability of intestinal mucosa or a candidate substance therefor. As an example, the object is to provide a technology for promoting the development of an LGS therapeutic drug, an LGS alleviating drug, and an intestinal mucosal permeability modulatory drug.

Solution to Problem

The invention according to the first aspect is directed to a diagnostic drug for evaluating permeability of intestinal mucosa, including chitin and/or chitosan as a main component.

The diagnostic drug may be used by oral administration or may be used by enema administration. A subject to be diagnosed may be other than a human.

The invention according to the second aspect is directed to a diagnostic drug for evaluating permeability of intestinal mucosa, including chitin and/or chitosan as a main component, the diagnostic drug being used by orally administering or enema administering the diagnostic drug to a test subject and measuring a blood concentration thereof after a lapse of a predetermined period of time.

The predetermined period of time only needs to be set as appropriate, and may be set to 30 minutes in the case of the oral administration and 5 minutes in the case of the enema administration.

The invention according to the third aspect is directed to a diagnostic drug according to the first or the second aspect of the present invention, wherein the chitin and/or chitosan has a weight average molecular weight prepared to a range of from 1,000 to 11,600.

Having a weight average molecular weight prepared to from 1,000 to 11,600 may be any of: (1) having an average molecular weight at any one value of from 1,000 to 11,600;

(2) having a plurality of average molecular weight peaks between 1,000 and 11,600; and (3) containing molecules having molecular weights of from 1,000 to 11,600 in an essentially uniform manner. In the case of (1), whether a substance having that molecular weight permeates the intestinal mucosa can be confirmed. In the case of (2), approximately how large the molecular weight of a substance that permeates the intestinal mucosa is can be accurately confirmed by a single test using an agent having a small half-width of each peak. Also in the case of (3), approximately how large the molecular weight of a substance that permeates the intestinal mucosa is can be confirmed by a single test.

The invention according to the fourth aspect is directed to a diagnostic drug according to the second aspect of the present invention, wherein a dose of the diagnostic drug is set to a range of from 8.33 mg to 20.83 mg per kg of body weight.

The intake is smaller than that in a lactulose-mannitol test, and hence a burden on the test subject can be reduced.

The invention according to the fifth aspect is directed to a diagnostic method, including: orally administering or enema administering chitin and/or chitosan to an animal, the animal being other than a human; and measuring a concentration of the administered substance in blood after a lapse of a predetermined period of time, to thereby evaluate permeability of intestinal mucosa of the animal.

The concentration of the administered substance means: a chitin concentration when only chitin is administered; a chitosan concentration when only chitosan is administered; and the concentration of a mixture of chitin and chitosan when the mixture of chitin and chitosan is administered.

The invention according to the sixth aspect is directed to a diagnostic method, including: orally administering or enema administering chitin and/or chitosan to a test subject; and measuring a concentration of the administered substance in blood after a lapse of a predetermined period of time, to thereby evaluate permeability of intestinal mucosa of the test subject.

The invention according to the seventh aspect is directed to a diagnostic method according to the 5th or the 6th aspect of the present invention, wherein the chitin and/or chitosan has a weight average molecular weight prepared to a range of from 1,000 to 11,600.

The invention according to the eighth aspect is directed to a diagnostic method according to the 6th aspect of the present invention, wherein an oral dose of the chitin and/or chitosan is set to a range of from 8.33 mg to 20.83 mg per kg of body weight.

The invention according to the ninth is directed to a use of chitin and/or chitosan, for evaluation of permeability of intestinal mucosa through oral administration and blood concentration measurement after a lapse of a predetermined period of time, or through enema administration and blood concentration measurement after a lapse of a predetermined period of time.

The chitin and/or chitosan preferably has a weight average molecular weight prepared to a range of from 1,000 to 11,600.

The dose is preferably set to a range of from 8.33 mg to 20.83 mg per kg of body weight in the case of a human.

The invention according to the 10th aspect is directed to a food and drink evaluation method, including: allowing a test subject to eat and drink a single or a plurality of specific foods and drinks; allowing the test subject to orally ingest chitin and/or chitosan during the eating and drinking, or before or after the eating and drinking; and measuring a concentration of the ingested substance in blood after a lapse of a predetermined period of time from the oral ingestion, to thereby determine whether the foods and drinks have a potential to serve as a factor affecting permeability of intestinal mucosa of the test subject.

The chitin and/or chitosan preferably has a weight average molecular weight prepared to a range of from 1,000 to 11,600.

The intake is preferably set to a range of from 8.33 mg to 20.83 mg per kg of body weight.

The term "affect" includes both increasing and reducing the permeability or leakiness of the intestinal mucosa. With regard to LGS, increasing the leakiness means inducing or aggravating LGS, and reducing the leakiness means inhibiting, alleviating, ameliorating, or curing LGS.

From the viewpoint of the inhibition of LGS, examples of the specific single food and drink may include yogurt and a whey beverage. Along with this, an objective performance index for a food touted as a conditioner for gut flora can also be provided.

From the viewpoint of the induction of LGS, examples of the plurality of specific foods and drinks may include: an oyster and wine; and a pork steak and beer.

According to the present invention, screening of an inducer or an inhibitor can be performed for an individual.

The term "before or after the eating and drinking" may mean, for example, a time point 20 minutes before the start of the eating and drinking or a time point 15 minutes after the end of the eating and drinking.

The invention according to the 11th is directed to a food and drink evaluation drug, including chitin and/or chitosan as a main component, the food and drink evaluation drug being used by: allowing a test subject to eat and drink a single or a plurality of specific foods and drinks; allowing the test subject to orally ingest chitin and/or chitosan during the eating and drinking, or before or after the eating and drinking; and measuring a concentration of the ingested substance in blood after a lapse of a predetermined period of time from the oral ingestion, to thereby determine whether the foods and drinks have a potential to serve as a factor affecting permeability of intestinal mucosa of the test subject.

The chitin and/or chitosan preferably has a weight average molecular weight prepared to a range of from 1,000 to 11,600.

The intake is preferably set to a range of from 8.33 mg to 20.83 mg per kg of body weight.

The invention according to the 12th aspect is directed to an evaluation method, including: administering a given substance; separately orally administering or enema administering chitin and/or chitosan; and measuring blood concentrations of the orally administered substance or the enema administered substance before and after the administration of the given substance, to thereby evaluate whether the given substance has a normalizing action on permeability of intestinal mucosa, and how strong the normalizing action, when present, is.

A subject to which the given substance is administered may be a human or may be an animal other than a human.

The chitin and/or chitosan preferably has a weight average molecular weight prepared to a range of from 1,000 to 11,600.

An oral dose or enema dose is preferably set to a range of from 8.33 mg to 20.83 mg per kg of body weight in the case of a human.

The invention according to the 13th aspect is directed to an evaluation agent, including chitin and/or chitosan as a main component, to be orally administered or enema administered separately from a given substance to be administered, the evaluation agent being used for evaluating whether the given substance has a normalizing action on permeability of intestinal mucosa, and how strong the normalizing action, when present, is, through measurement of blood concentrations of the evaluation agent before and after the administration of the given substance.

A subject to which the given substance is administered may be a human or may be an animal other than a human.

The chitin and/or chitosan preferably has a weight average molecular weight prepared to a range of from 1,000 to 11,600.

The dose is preferably set to a range of from 8.33 mg to 20.83 mg per kg of body weight in the case of a human.

The invention according to the 14th aspect is directed to a diagnostic device, including: concentration-measuring means for measuring a concentration of chitin and/or chitosan in blood collected from a test subject; and evaluation means for evaluating permeability of intestinal mucosa of the test subject on the basis of the concentration measured by the concentration-measuring means.

The diagnostic device may also be called an intestinal mucosal permeability evaluation device.

Advantageous Effects of Invention

According to the present invention, the degree of permeability of the intestinal mucosa can be directly evaluated with high reliability.

In addition, according to the present invention, a food and drink that affects the permeability of the intestinal mucosa can be determined.

In addition, according to the present invention, an objective evaluation of a pharmaceutical for normalizing the permeability of the intestinal mucosa or a candidate substance therefor can be performed.

DESCRIPTION OF EMBODIMENTS

Construction of LGS-induced Models

In this embodiment, LGS was assumed as an example in which the leakiness of an intestinal tract was evaluated, and first, induction tests therefor were performed.

One model uses aspirin and omeprazole (hereinafter referred to as "AO model" as appropriate). Conditions were modified on the basis of the literature (Innate Immun. 2015 July;21(5):537-45).

An outline of the test is as follows: per kg of body weight of mice, 100 mg of aspirin (100 mg/kg) is orally administered twice a day for 6 days and 10 mg of omeprazole (10 mg/kg) is intraperitoneally administered twice a day for 6 days, and the degree of LGS is measured on the 7th day.

Another model is an intestinal tract ischemia-reperfusion model (hereinafter referred to as "IR model" as appropriate). Conditions were modified on the basis of the literature (Gastroenterology. 2001 February;120(2):460-9.) and the like.

An outline of the test is as follows: an intestinal tract is clipped continuously for 30 minutes to be brought into an ischemia state, and then unclipped to achieve reperfusion, and 30 minutes later, the degree of LGS is measured. As an expression specifying an ischemia time of 30 minutes, this model is referred to as "IR 30) model" as appropriate.

Figure 1:
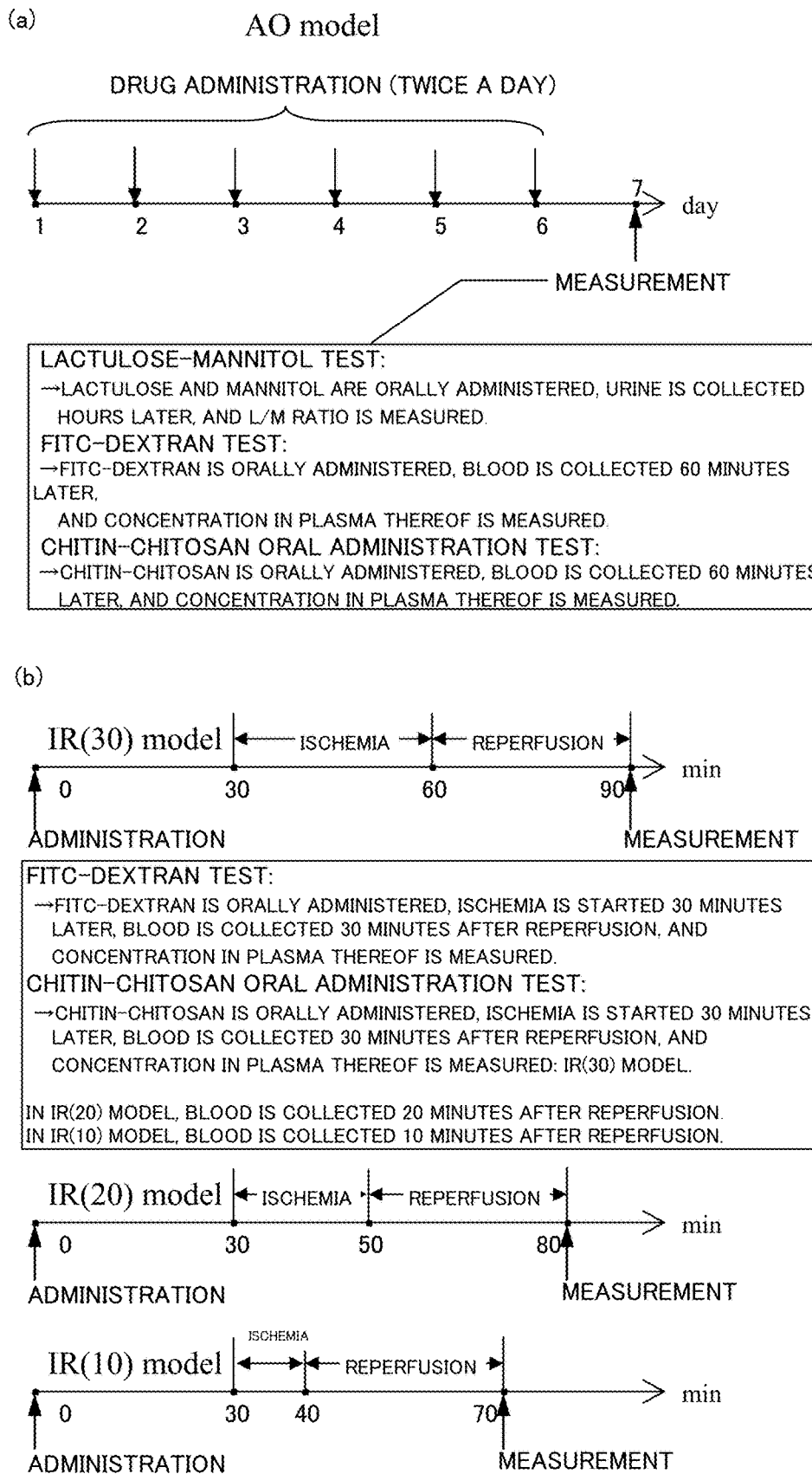
FIG. 1 are test outlines of an AO model and an IR model.

Outlines of both models are illustrated in FIG. 1. In FIG. 1b, an IR(20) model and an IR(10) model, which are described later, are also illustrated.

Figure 2:
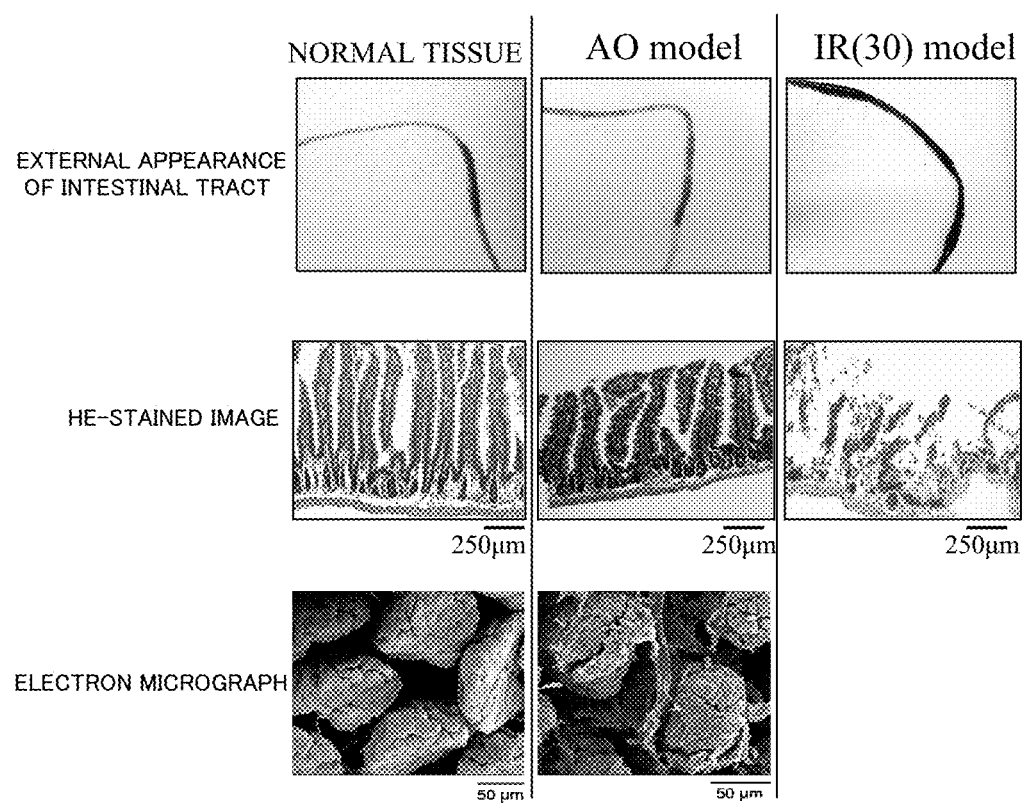
FIG. 2 are photographs for showing a normal state of an intestinal tract and an LGS-induced state thereof.

In FIG. 2, external appearance photographs, HE-stained images, and electron micrographs of the intestinal tract are shown. As compared to a normal tissue, in the AO model, cracks are found in intestinal villi, and hence the occurrence of mild LGS is recognized. In addition, in the IR(30) model, intestinal villi are significantly damaged, and hence the occurrence of severe LGS is recognized.

Evaluation of Degree of LGS

The above-mentioned models were used to determine leakiness based on a difference in molecular weight.

Figure 3:
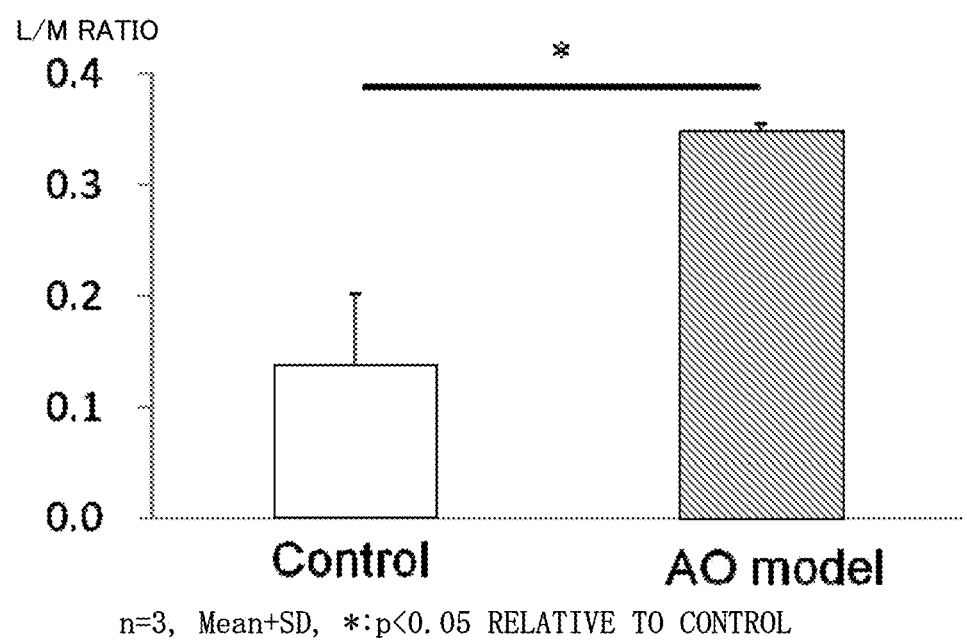
FIG. 3 is a graph for showing the results of a lactulose-mannitol test for the AO model.

First, a lactulose-mannitol test was performed for the AO model. Lactulose and mannitol were both orally administered at 500 mg/kg, urine was collected for 4 hours, and an L/M ratio was measured. The results are shown in FIG. 3. As compared to mice administered with none of aspirin and omeprazole and not having LGS induced, i.e., a control, the AO model had an about 2-fold increase in L/M ratio. It was able to be confirmed from the foregoing that a state in which the leakiness of a substance having a molecular weight of more than 300, such as mannitol, was raised was found.

Figure 4:
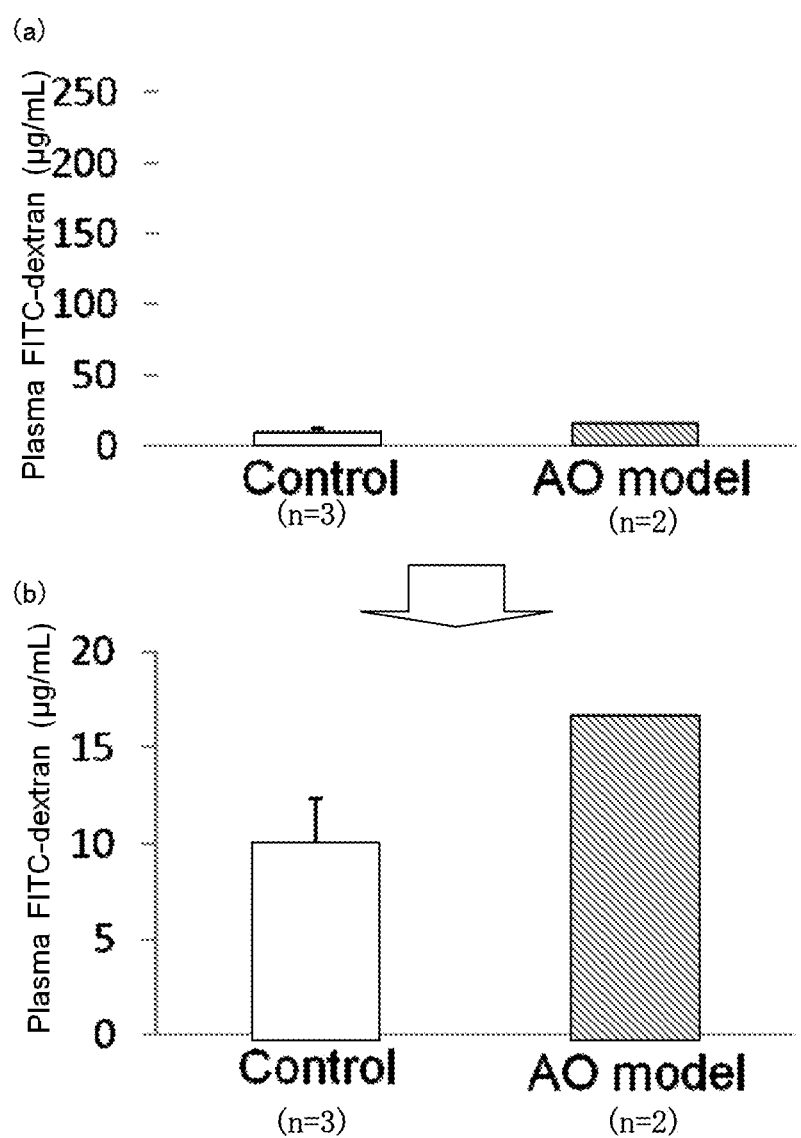
FIG. 4 are graphs for showing the results of an FITC-dextran test for the AO model.

Next, an FITC-dextran test was performed for the AO model. FITC-dextran was orally administered at 600 mg/kg, blood was collected 60 minutes later, and the concentration in plasma thereof was measured. The results are shown in FIGS. 4. It was able to be confirmed that the concentration of dextran in the plasma was increased to some degree as compared to the control (FIG. 4b).

Figure 5:
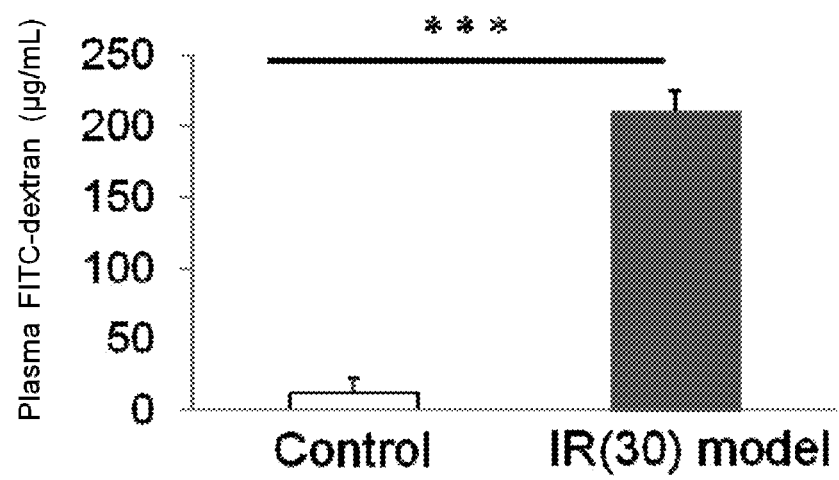
FIG. 5 is a graph for showing the results of an FITC-dextran test for the IR model.

In addition, an FITC-dextran test was performed for the IR(30) model. FITC-dextran was orally administered at 600 mg/kg, ischemia was started 30 minutes later, blood was collected 30 minutes after reperfusion, and the concentration in plasma thereof was measured. The results are shown in FIG. 5. The dextran concentration in plasma had an increase as high as about 15-fold as compared to the control.

As apparent from a comparison between FIG. 4a and FIG. 5, the IR(30) model may be said to be a model capable of inspecting a state in which a substance having a large molecular weight is allowed to migrate to blood more easily, as compared to the AO model. In other words, the IR (30) model may be said to be a model capable of evaluating severe LGS.

On the other hand, on the basis of a comparison between FIG. 3 and FIG. 4b, the AO model may be said to be a model capable of inspecting a state that is not so severe as to allow a substance having a large molecular weight to easily migrate to blood. In other words, the AO model may be said to be a model capable of evaluating mild LGS.

Evaluation of LGS using Chitin-Chitosan

Next, evaluation of LGS using chitin-chitosan was performed.

First, the shell of a crab was deproteinized, decalcified, and deacetylated to provide a mixture of chitin and chitosan. Subsequently, the mixture of chitin and chitosan was decomposed into small molecules to provide a chitin-chitosan sample having a weight average molecular weight of 7,900. As a method for the decomposition into small molecules, which is not particularly limited, there are given a method involving hydrolyzing the mixture of chitin and chitosan with concentrated hydrochloric acid (JP 5714963 B2), and a method involving dissolving the mixture with hydrochloric acid or an organic acid, such as acetic acid, citric acid, or lactic acid, and then decomposing the mixture into small molecules using a chitosanase enzyme (JP 2013-79217 A).

Next, for the AO model, 2.50 mg of the above-mentioned sample was orally administered on the 7th day, blood was collected 60 minutes later, and the concentration of chitin-chitosan in plasma was measured (see FIG. 1a).

In addition, for the IR(30) model, 2.50 mg of the above-mentioned sample was orally administered 30 minutes before the start of ischemia, blood was collected 30 minutes after reperfusion, and the concentration of chitin-chitosan in plasma was measured (see FIG. 1B).

For the measurement, first, the plasma was extracted from the blood by a conventional method, and chitin-chitosan in the plasma was decomposed into chitose (2,5-anhydro-D-mannose) serving as a constituent monosaccharide by a nitrous acid decomposition method. Next, its aldehyde group was allowed to react with 3-methyl-2-benzothiazolinone hydrazone hydrochloride (MBTH) and iron (III) chloride to develop a blue color. Finally, the degree of the blue color was measured with an absorbance meter, and the concentration was calculated on the basis of the dye amount.

Figure 6:
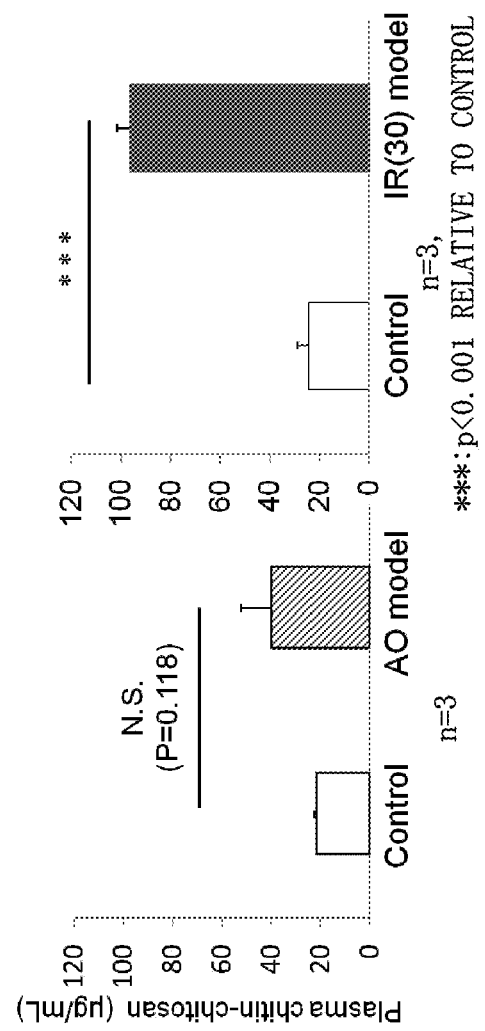
FIG. 6 are graphs for showing the measurement results of chitin-chitosan concentrations for the AO model and the IR model.

The results are shown in FIGS. 6. As shown in FIG. 6, it can be confirmed that chitin-chitosan is allowed to migrate into the blood more remarkably in the IR(30) model than in the AO model. This means a larger molecular weight of the sample used, and agrees with the relationship between FIG. 4b and FIG. 5.

In view of the foregoing, the inventors of the present invention have decided to investigate the applicability of the chitin-chitosan as a diagnostic drug for the degree of LGS, and by extension, a diagnostic drug for diagnosing permeability of intestinal mucosa (evaluation drug for evaluating permeability of intestinal mucosa). The concentration evaluation has been performed with the absorbance in the foregoing, but is not limited thereto, and chitin and chitosan do not particularly need to be distinguished from each other as long as the blood concentration can be detected. Therefore, in the present invention, the expression "chitin-chitosan" is used, and means chitin and/or chitosan.

Figure 7:
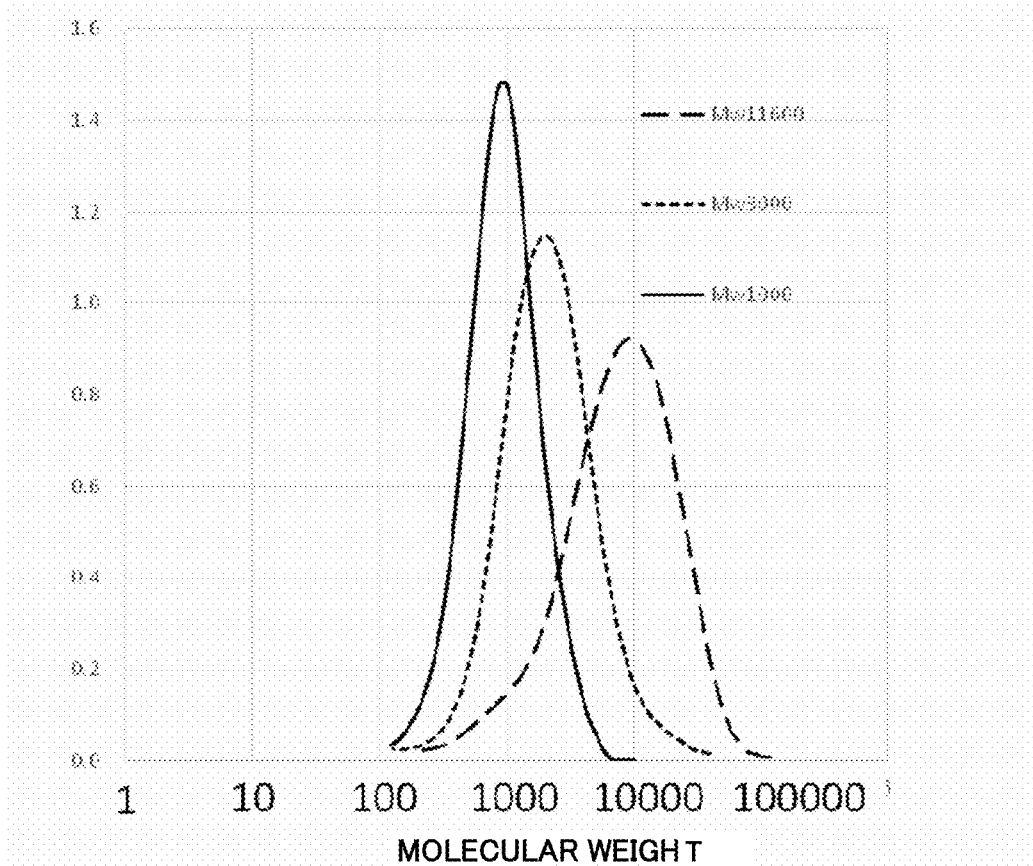
FIG. 7 is a graph for showing the manner of distribution of samples containing chitin-chitosan having weight average molecular weights of 1,000, 3,000, and 11,600 as main components.

First, a solution of hydrochloric acid or an organic acid was prepared, and the chitin-chitosan sample having a weight average molecular weight of 7,900 was fractionated using UF membranes (having molecular weight cut-offs of 3,000, 6,000, 10,000, and the like) into chitin-chitosan having weight average molecular weights of 1,000, 3,000, 7,900, and 11,600. In FIG. 7, the manner of distribution of the prepared samples is shown. In addition, a measurement method for the weight average molecular weight is also described.

Next, for the IR model, 2.5 mg each of the above-mentioned samples was orally administered, and the blood concentration of the chitin-chitosan was measured. It was considered that an ischemia time of 30 minutes caused excessively large damage to an intestinal tract, and hence, in this case, a test was performed with the ischemia time shortened to 20 minutes. This model is referred to as "IR(20) model".

Figure 8:
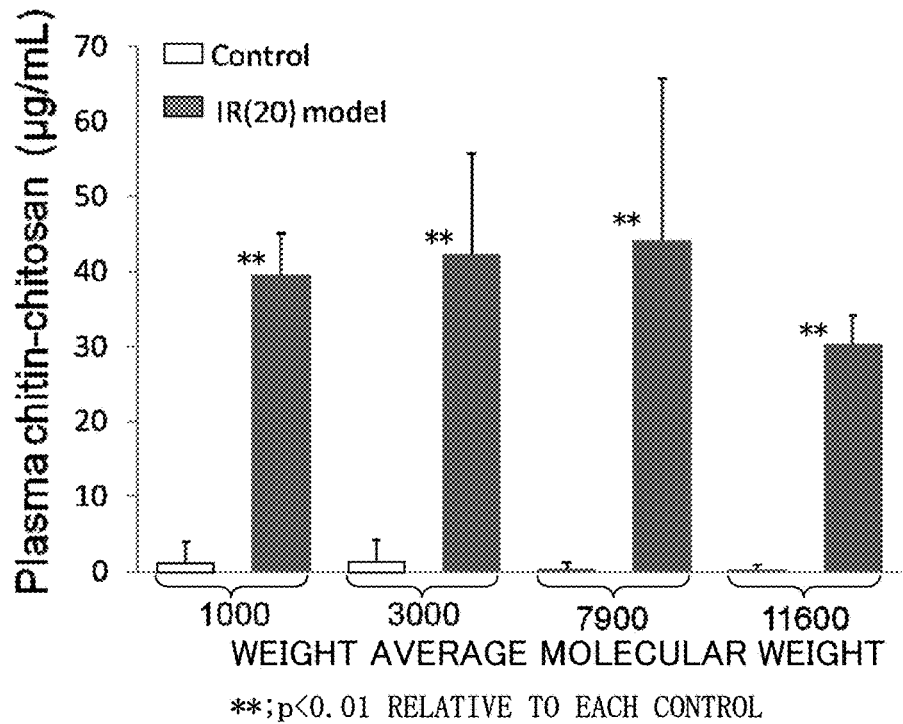
FIG. 8 is a graph for showing the blood concentrations of chitin-chitosan at various molecular weights for the IR(20) model.

For the IR(20) model, the measurement results of the blood concentrations of the chitin-chitosan at various molecular weights are shown in FIG. 8. In FIG. 8, the results of a control, i.e., without ischemia-reperfusion are also shown. As apparent from FIG. 8, although the concentration at a weight average molecular weight of 11,600 is slightly small, in general, the sample having any molecular weight has migrated into blood.

In view of the foregoing, the ischemia time was changed to 10 minutes to further reduce the degree of LGS, inducing medium-degree LGS, and sample-screening performance was investigated. This test is referred to as "IR(10) model".

Figure 9:
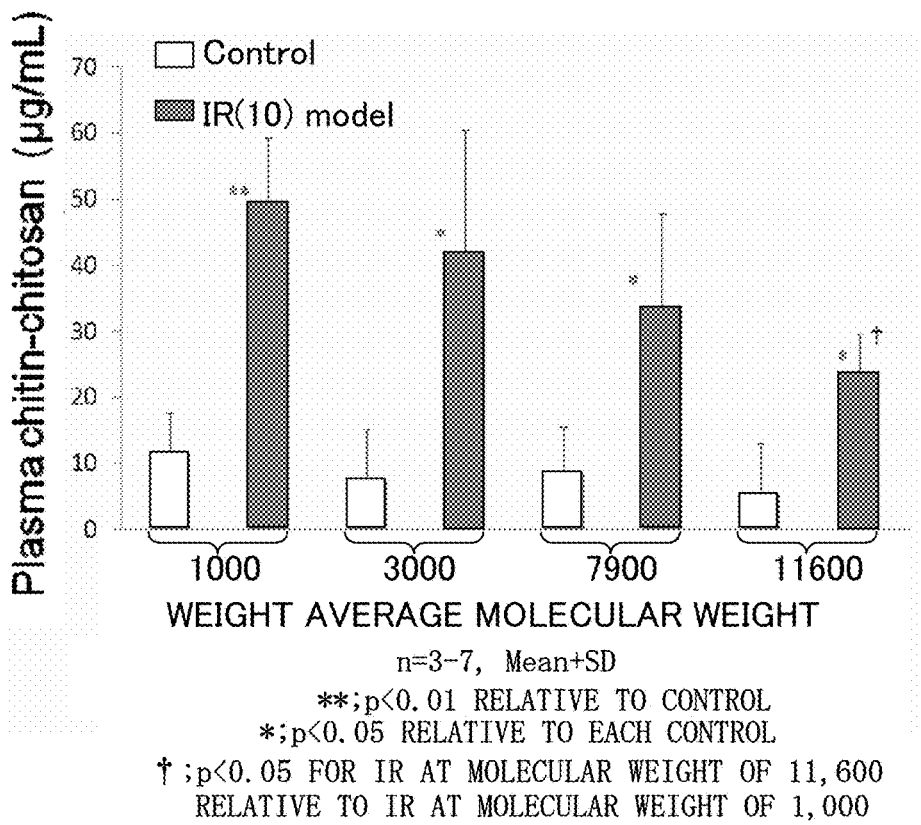
FIG. 9 is a graph for showing the blood concentrations of chitin-chitosan at various molecular weights for the IR(10) model.

For the IR(10) model, the measurement results of the blood concentrations of the chitin-chitosan at various molecular weights are shown in FIG. 9. As can be seen in FIG. 9, it can be confirmed that a sample having a smaller weight average molecular weight is more liable to leak, and a sample having a larger weight average molecular weight is less liable to leak.

As apparent from the above-mentioned experiments, through the use of the chitin-chitosan, evaluation can be performed regarding the following: how large the molecular weight of a substance that leaks through the intestinal tract is; and a state in which a substance having how large a molecular weight leaks through the intestinal tract to what degree is found.

That is, the chitin and/or chitosan can be used for evaluation of permeability of intestinal mucosa through oral administration and blood concentration measurement after a lapse of a predetermined period of time.

In other words, it may be said that a diagnostic drug for evaluating permeability of intestinal mucosa, containing chitin and/or chitosan as a main component, was able to be obtained.

In addition, it may also be said that a diagnostic drug for evaluating permeability of intestinal mucosa, containing chitin and/or chitosan as a main component, the diagnostic drug being used by allowing a test subject to orally ingest the diagnostic drug and measuring a blood concentration thereof after a lapse of a predetermined period of time, was able to be obtained.

It may also be said that an evaluation technology for an increase in intestinal mucosal permeability was able to be obtained.

As shown in FIG. 8 and FIG. 9, the IR model can induce LGS of any degree from mild to severe through the adjustment of the ischemia time, and may be said to be a model capable of constructing a versatile and objective evaluation system.

Figure 10:
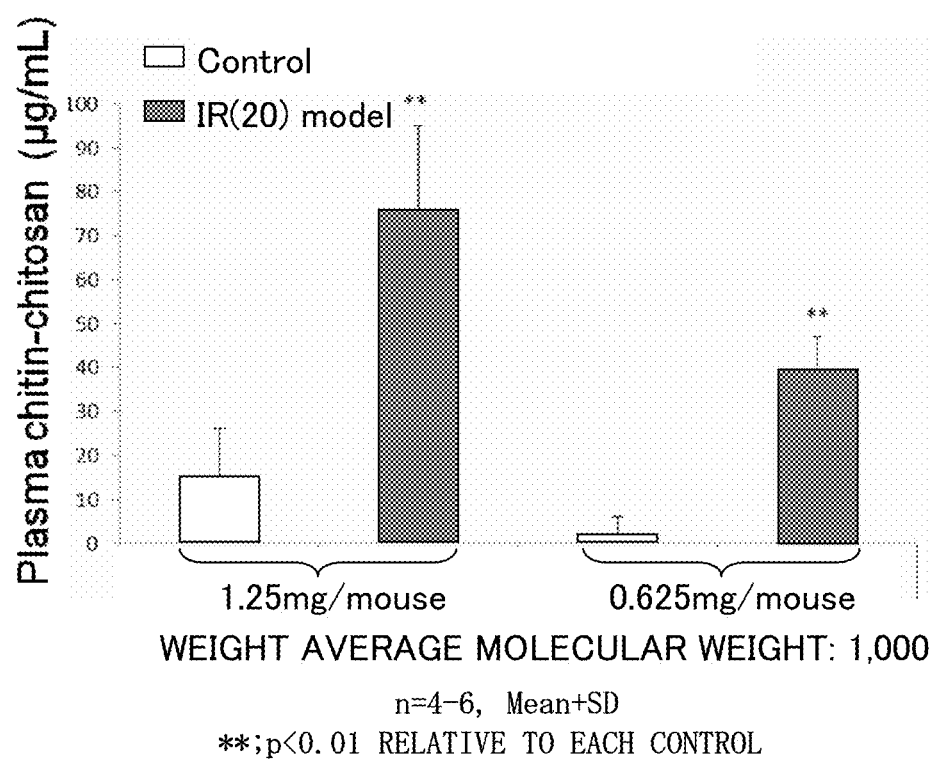
FIG. 10 is a graph for showing results for the IR(20) model obtained by orally administering a diagnostic agent having a weight average molecular weight of 1,000 at each of 1.25 mg/mouse and 0.625 mg/mouse, and measuring its blood concentration.

For the IR(20) model, a diagnostic drug having a weight average molecular weight of 1,000 was orally administered at each of 1.25 mg/mouse and 0.625 mg/mouse, and a blood concentration in the case where the dose was reduced was measured. The results are shown in FIG. 10. As apparent from FIG. 10, it was found that significant concentration measurement was possible even at 0.625 mg/mouse. When this value is converted for a human having a body weight of 60 kg, the dose of the diagnostic drug is 1.25 g. In addition, in terms of measurement limit taking also a control into consideration, significant concentration measurement is in theory possible even at 0.500 g of oral ingestion for a 60 kg human. That is, it is appropriate that the dose or the intake be set to a range of from 8.33 mg to 20.83 mg per kg of body weight. In consideration of individuals ranging from a child having a body weight of 5 kg to an adult having a body weight of 200 kg, it may be said that the oral intake may be set to a range of from 0.04 g to 4.20 g. In any case, an oral intake of as much as 15 g required in the lactulose-mannitol test is not required, and hence the diagnostic drug may be said to relieve a burden on the test subject.

It is considered that the same applies to the case of enema administration.

Figure 11:
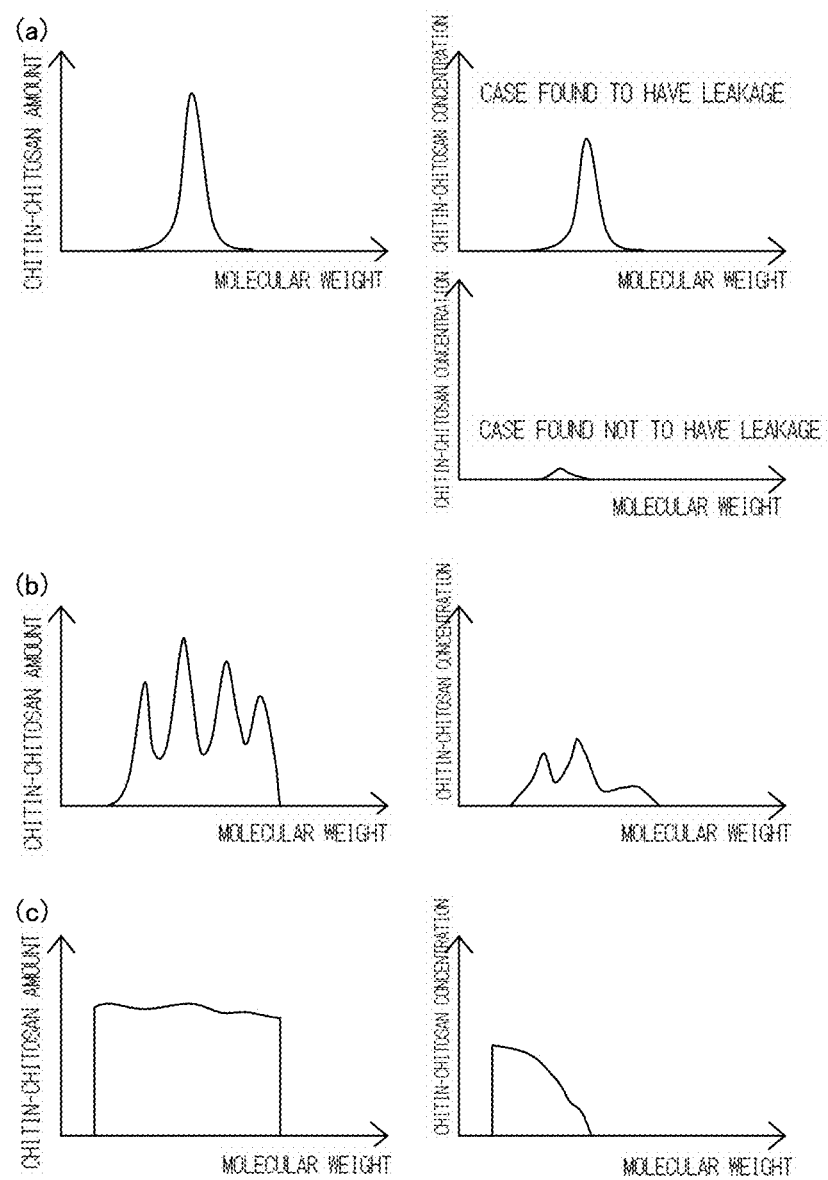
FIG. 11 are schematic diagrams of distribution modes of the molecular weight of a diagnostic drug and concentration measurement results.

In addition, although depending on a detection system, it is preferred that the diagnostic drug have a weight average molecular weight prepared to a range of from 200 to 20,000, more preferably from 1,000 to 11,600. FIG. 11 are schematic diagrams of distribution modes of the molecular weight of the diagnostic drug and concentration measurement results. In FIG. 11a, a single-peak diagnostic drug is shown. Whether a state in which a substance having at least up to this molecular weight leaks is found can be determined. In FIG. 11b, a multi-peak diagnostic drug is shown. How large the maximum molecular weight of a substance that is liable to leak is can be determined. In FIG. 11c, a diagnostic drug having a uniform spread of molecular weights is shown. Also in this case, how large the maximum molecular weight of a substance that is liable to leak is can be determined.

The diagnostic drug or diagnostic method described above has the following advantages.

Having no toxicity (Usable for a human. Allowing an animal experiment as well.).
Orally administrable.
Not produced in a living body including an intestine (Allowing direct concentration measurement.).
Not easily decomposed in a living body (Allowing direct concentration measurement.).
Hardly absorbed from an intestinal tract in a normal state.
Allowing the adjustment of a molecular weight.

Test Using Highly Purified Chitin-Chitosan

Figure 12:
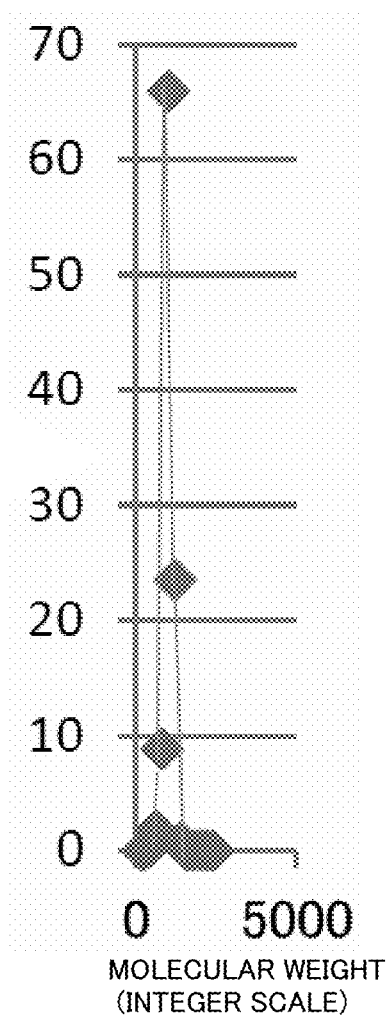
FIG. 12 is a graph for showing the manner of molecular weight distribution of a purified sample.

Next, a test was performed using chitin-chitosan having a sharper molecular weight distribution. FIG. 12 is a graph for showing the manner of molecular weight distribution of a chitin-chitosan sample used in the following test. The sample is a highly purified sample which has a sharp distribution as compared to FIG. 7, and in which, according to the results of separate analysis, molecules having molecular weights of from 823 to 1,984 (having molecular weights of from about 1,000 to about 1,200 as hydrochlorides) account for 98 wt % of the entirety. This sample is referred to as "purified sample" as appropriate.

Figure 13:
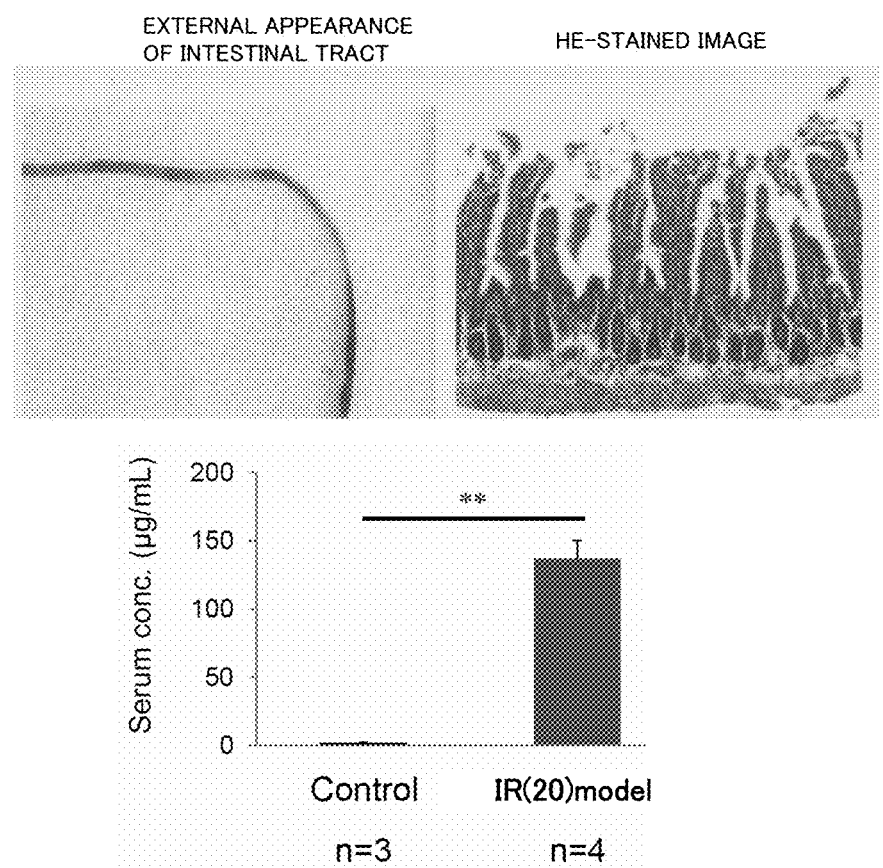
FIG. 13 are a graph for showing the measurement results of a chitin-chitosan concentration using the purified sample, and the external appearance of an intestinal tract and an HE-stained image, for the IR(20) model.

For the IR(20) model, a chitin-chitosan concentration in serum was measured using the purified sample. The measurement results, and the external appearance of an intestinal tract and an HE-stained image thereof are shown in FIG. 13. It is found from the HE-stained image that a mucosal disorder has only slightly advanced, but as with FIG. 8, it can be confirmed that a state in which chitin-chitosan having a molecular weight of about 1,000 leaks into blood is found.

Safety Confirmation

Figure 14:
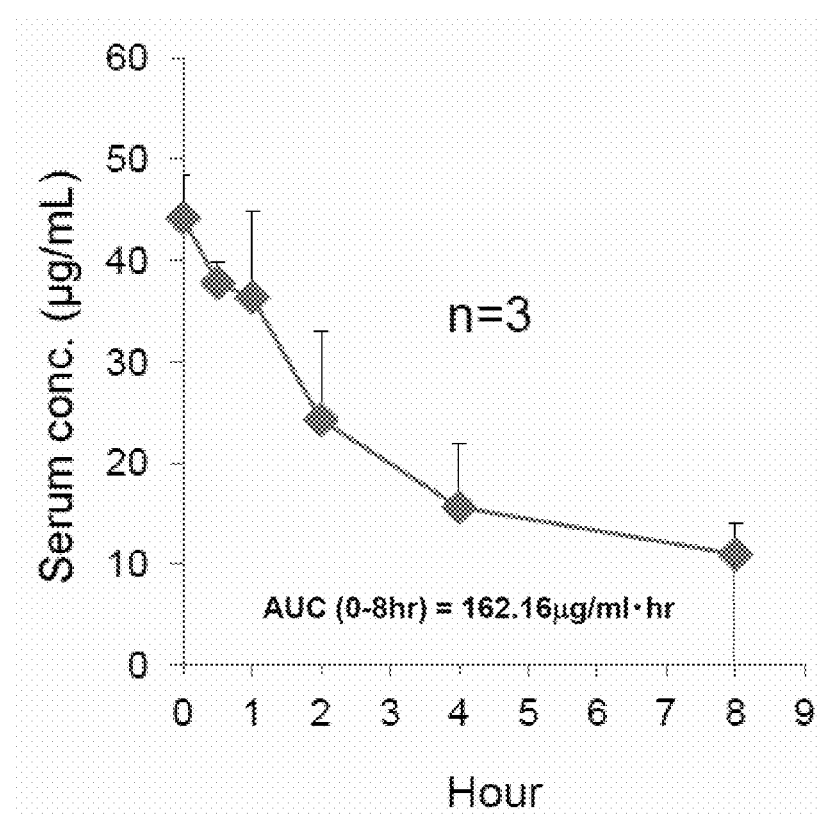
FIG. 14 is a graph of the measurement of a temporal change in chitin-chitosan amount in circulating blood in the IR(10) model in which the purified sample was orally administered to mice.

In the IR(10) model in which the purified sample was orally administered to mice, a temporal change in chitin-chitosan amount in circulating blood was measured. A temporal change from 30 minutes after reperfusion is shown in FIG. 14. An oral dose was set to 2.5 mg/mouse.

The circulating blood amount of a mouse is estimated to be an amount corresponding to $\frac{1}{13}$ of its body weight, and hence the amount is 1.93 ml when the body weight is 25 g. Meanwhile, the Area Under the Curve (AUC) shown in FIG. 14 was 162.16 μg/ml between 0 h and 8 h. Therefore, the amount of the chitin-chitosan that leaked into circulating blood in 8 hours is 162.16*1.93=312.97 μg. It may be said from the foregoing that 12.5% of the oral dose of the purified sample leaked into circulating blood (312.97 μg/2.5 mg=0.125) . The mice remained alive even after 8 hours.

Figure 15:
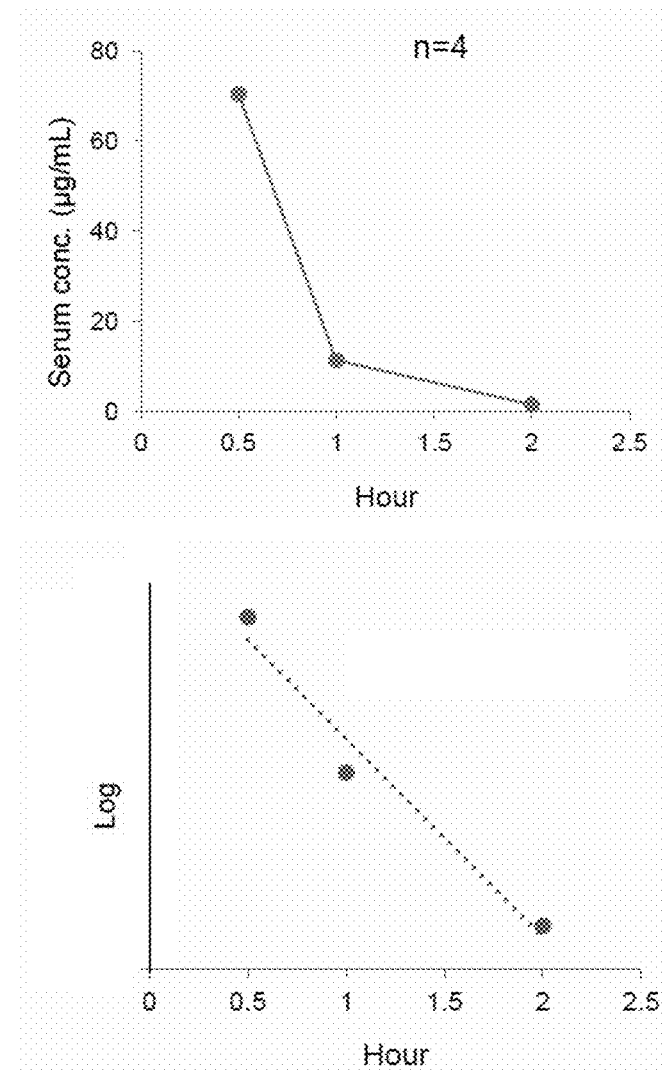
FIG. 15 are graphs of the measurement of a temporal change in blood concentration of chitin-chitosan in the case where the purified sample was intravenously administered to mice not subjected to ischemia-reperfusion treatment.

In addition, 2.5 mg of the purified sample was intravenously administered to nontreated mice, i.e., mice not subjected to ischemia-reperfusion treatment, and a temporal change in blood concentration of the chitin-chitosan was measured. The measurement results are shown in FIG. 15. It was confirmed that the blood concentration was about 70 μg/ml even when the intravenous administration was performed (the blood concentration estimated by extrapolation was about 150 μg/ml even immediately after the administration), and the chitin-chitosan rapidly disappeared from the blood in about 2 hours (the concentration decrease was linear when replotted on a logarithmic scale). This is considered to be due to renal excretion. No shock symptom due to the intravenous administration was found, and the mice remained alive even after 2 hours.

The following may be said in consideration of the two tests.
1) The mice continued to live even after the tests, and hence it was able to be confirmed again that the chitin-chitosan was safe for a living body (at least the possibility of immediately seriously affecting the living body is extremely low).
2) The chitin-chitosan can be said to be safe to a living body also because of rapid disappearance thereof from the blood.
3) Under the above-mentioned conditions, the chitin-chitosan in the blood was detected from the blood even after 8 hours. Accordingly, the chitin-chitosan allows concentration measurement even after a lapse of some time from administration, and hence is useful as a diagnostic drug/evaluation drug. In addition, a temporal change can also be grasped.
4) The chitin-chitosan rapidly disappears after leaking into blood, and hence, through oral administration or enema administration thereof, a real-time state of the leakiness or permeability of an intestine can be grasped. More simply, it may be said that the state of the intestine can be grasped.

Permeability Evaluation with Model other than IR Model

Next, evaluation of permeability or leakiness was performed for models other than the above-mentioned evaluation test involving directly applying a load to the intestine like ischemia-reperfusion.

Permeability Evaluation with Food Allergy Model

Figure 16:
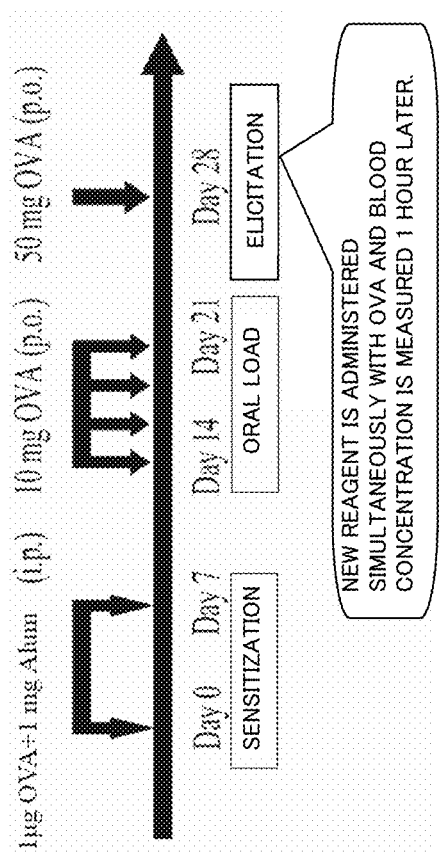
FIG. 16 is an explanatory diagram for illustrating a protocol for inducing OVA allergy.

First, mucosal permeability evaluation of the small intestine was performed for mice having egg allergy, i.e., OVA-IgE mice. A protocol for inducing OVA allergy is as illustrated in FIG. 16. First, mice were sensitized by being intraperitoneally administered with ovalbumin (OVA), followed continuously by oral administration therewith. 28 Days after the sensitization, the mice were orally administered with OVA and the purified sample and evaluated. In the OVA-IgE mice, severe diarrhea, a typical symptom of food allergy, was found.

Figure 17:
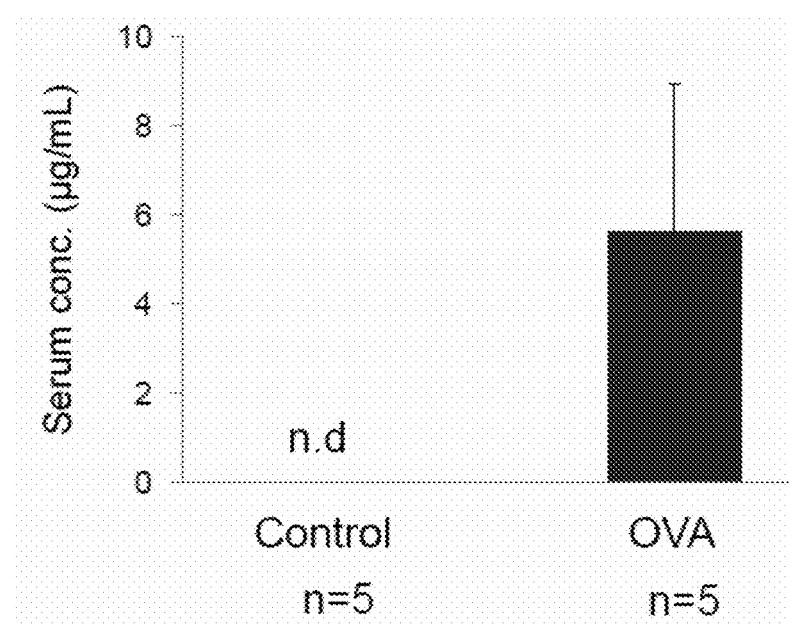
FIG. 17 is a graph for showing the blood concentration of chitin-chitosan using OVA-IgE mice.

The blood concentration measurement results of the chitin-chitosan are shown in FIG. 17. For comparison, the results of a lactulose-mannitol test are also shown. As shown in FIG. 17, it was able to be found that, when diarrhea resulting from food allergy occurred, a state in which the permeability of the intestine was raised was found. It was also found that the raising of permeability was able to be more clearly judged by the evaluation than by the lactulose-mannitol test.

Permeability Evaluation with High-fat Diet Model and NASH-inducing Diet Model

Next, permeability evaluation was performed for mice kept fed with a high-fat diet and a nonalcoholic steatohepatitis (NASH)-inducing diet, respectively.

The components of the high-fat diet and the NASH-inducing diet are as shown below.

TABLE 1

|  | High-fat diet | NASH-inducing diet |
|---|---|---|
|  | (g/100 g of feed) | |
| Carbohydrate | 26 | 45 |
| Protein | 26 | 22 |
| Lipid | 35 | 20 |

Cholesterol amounts in the lipid and fructose amounts in the carbohydrate are as shown below.

|  | High-fat diet | NASH-inducing diet |
|---|---|---|
|  | (g) | |
| Cholesterol in lipid | 0.028 | 2 |
| Fructose in carbohydrate | 0 | 22 |

High-fat diet model: 6-Week-old male C57BL/6 mice were allowed to ingest the high-fat diet ad libitum for 5 weeks, and then given neither water nor feed for 21 hours. After that, 2.5 mg of the purified sample was orally administered to the mice, and 1 hour after that, blood was collected from the inferior vena cava, and a chitin-chitosan amount was measured.

NASH-inducing diet model: 6-Week-old male C57BL/6 mice were allowed to ingest the NASH-inducing diet ad libitum for 4 weeks, and then given neither water nor feed for 21 hours. After that, 2.5 mg of the purified sample was orally administered to the mice, and 1 hour after that, blood was collected from the inferior vena cava, and a chitin-chitosan amount was measured.

Figure 18:
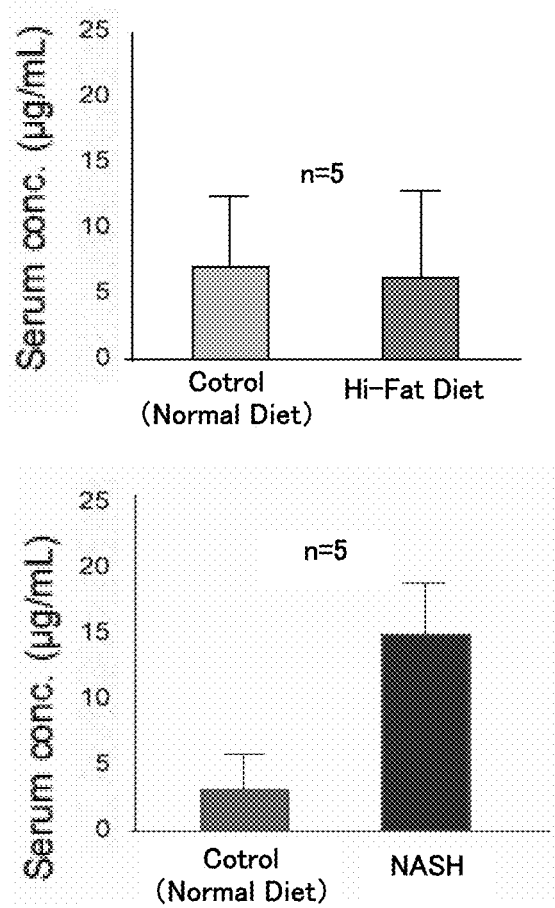
FIG. 18 are graphs for showing the blood concentrations of chitin-chitosan for a high-fat diet model and a NASH-inducing diet model.

The results are shown in FIG. 18. Although the permeability is not raised for the high-fat diet, the permeability is clearly raised in the case of the NASH-inducing diet. Thus, first, it has been able to be confirmed that it may be said that nonalcoholic steatohepatitis induces a state in which the permeability of the intestine is raised. Next, the leakiness of the intestine was not raised with the ingestion of the high-fat diet of the composition for the period of time. Thus, it has been found, conversely, that the use of the chitin-chitosan enables screening on how the intestine is affected by what diet.

Permeability Evaluation with DSS-induced Ulcerative Colitis Model

Next, permeability evaluation was performed for mice having ulcerative colitis induced with dextran sodium sulfate (DSS).

Ulcerative colitis model: First, mice were allowed to drink water having dissolved therein 2.5 wt % of DSS ad libitum. After 72 hours from the start of the ad libitum water drinking, the mice were enema administered or orally administered with the purified sample, and the blood concentrations of the chitin-chitosan were measured 1 hour after the administration for the mice subjected to the enema administration, and 4 hours after the administration for the mice subjected to the oral administration.

Figure 19:
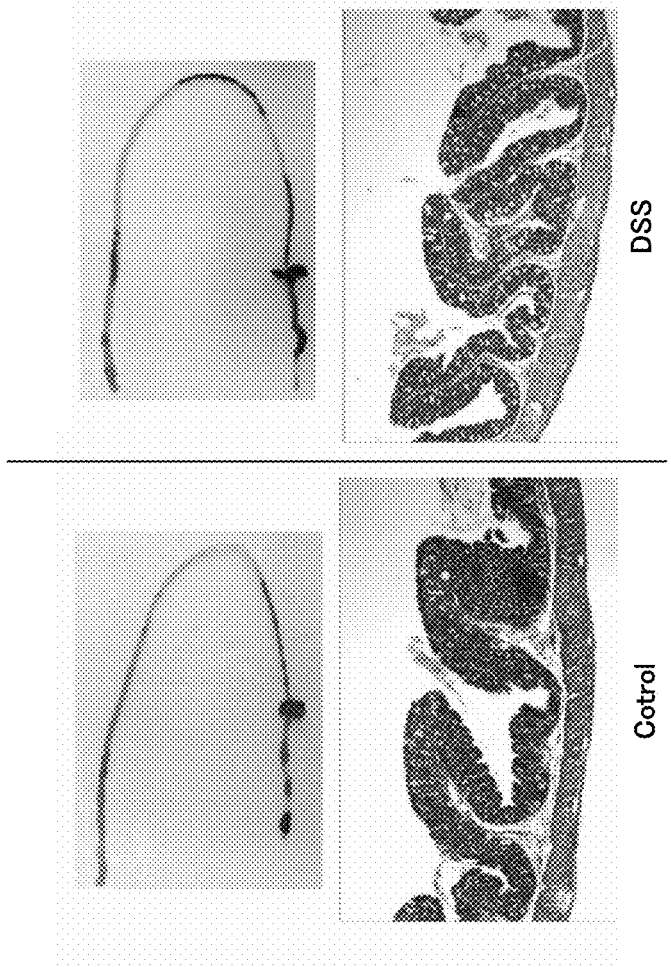
FIG. 19 are photographs for showing a whole intestine image and HE-stained image before onset in a DSS-induced ulcerative colitis model. Comparative images without the administration of DSS are also shown.

FIG. 19 are whole intestine images and HE-stained images of the case of allowing the drinking of water with DSS for 72 hours (3 days) and the case of not allowing water drinking. As shown in FIG. 19, at 72 hours from the start of the ad libitum water drinking, inflammation was not found in intestinal mucosa, and no clear change was observed anywhere across even the whole intestine.

Figure 20:
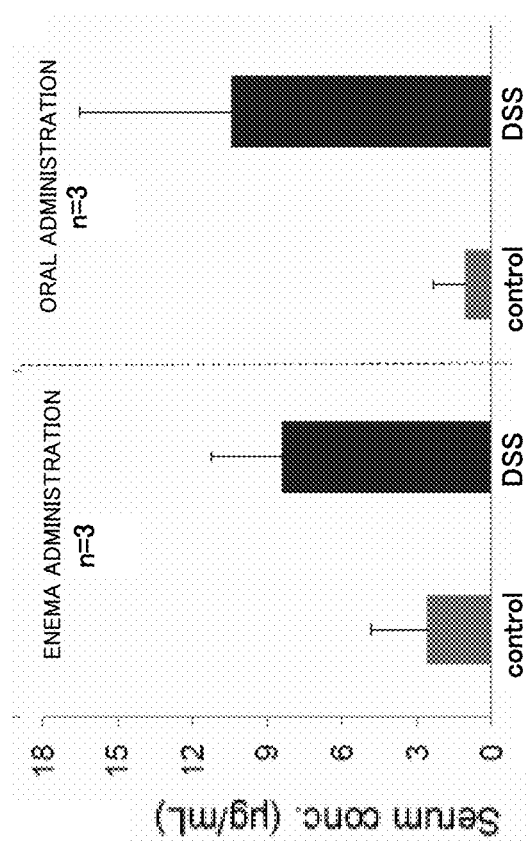
FIG. 20 is a graph for showing the blood concentrations of chitin-chitosan before onset in the DSS-induced ulcerative colitis model.

However, as shown in FIG. 20, in both the oral administration and the enema administration, leakage of the chitin-chitosan into blood was observed. In addition, as a result of continued observation, it was separately confirmed that the mice that had drunk water with DSS ad libitum developed inflammation 96 hours (4 days) after the start of the water drinking.

That is, surprisingly, it was able to be confirmed that the use of the chitin-chitosan enabled the detection of an abnormal increase in permeability of intestinal mucosa before the onset of ulcerative colitis.

Chitin-Chitosan as Evaluation Agent for Pharmacological Action

Figure 21:
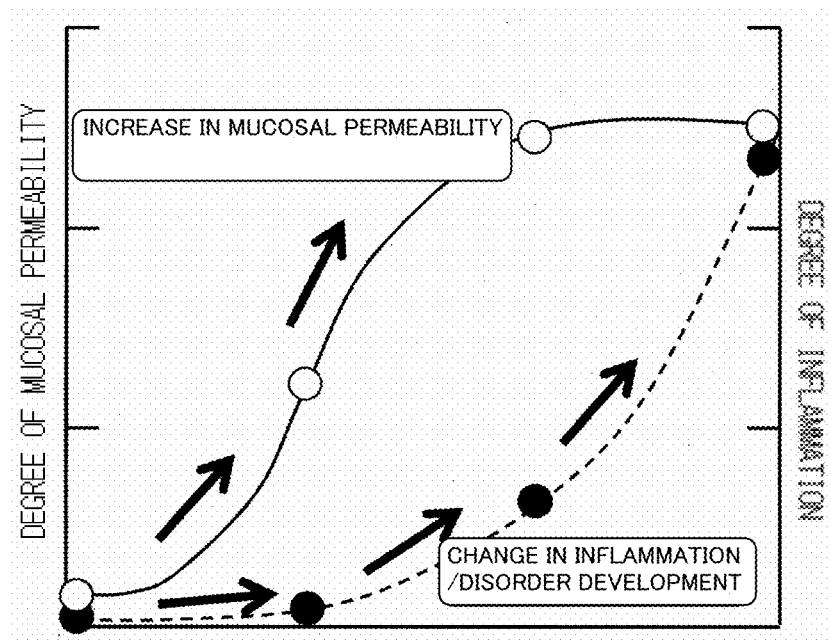
FIG. 21 is a conceptual diagram for illustrating a time lag between an increase in permeability of intestinal mucosa and the occurrence of inflammation or disorder.

As illustrated in FIG. 21, an increase in permeability of intestinal mucosa in general, not limited to that before the onset of ulcerative colitis, is considered to occur long before the occurrence of inflammation or disorder. Therefore, grasping of permeability or leakiness through the use of the chitin-chitosan enables pre-onset diagnosis, onset prevention, onset prediction, and evaluation of the pharmacological action of a therapeutic drug or the like.

First, in the case where inflammation is caused by food ingestion or the like, whereas it has hitherto been impossible to judge what is a causative food or a causative food group without continuing the ingestion until onset, the ingestion can be stopped before onset to relieve a burden and effective screening can be performed.

Next, the chitin-chitosan can also be used for screening for drug discovery of an LGS therapeutic drug, an LGS alleviating drug, an intestinal mucosal permeability modulatory drug, and the like. That is, by: administering a given substance (candidate substance); separately orally administering or enema administering chitin and/or chitosan; and measuring blood concentrations of chitin and/or chitosan before and after the administration of the candidate substance, it is possible to evaluate whether the candidate substance has a normalizing action on permeability of intestinal mucosa, and how strong the normalizing action, when present, is. The chitin-chitosan may also be provided as an evaluation agent containing chitin and/or chitosan as a main component, the evaluation agent being used as described above.

In addition, it also becomes possible to accumulate findings on inflammatory bowel diseases (IBDs), such as ulcerative colitis and Crohn's disease, and eosinophilic gastroenteritis. Findings on irritable bowel syndrome can also be accumulated. That is, it becomes possible to determine the active period or remission of pathology, determine a therapeutic effect and a drug efficacy evaluation, and predict pathology.

Application of Diagnostic Drug

In addition, when the results shown in FIG. 18 are also taken into consideration, the chitin-chitosan can also be used as an evaluation drug for a food and drink.

That is, by: allowing a test subject to eat and drink a single or a plurality of specific foods and drinks; allowing the test subject to orally ingest an evaluation drug containing the chitin-chitosan as a main component during the eating and drinking, or before or after the eating and drinking; and measuring a concentration of the chitin-chitosan in blood after a lapse of a predetermined period of time from the oral ingestion, it is possible to determine whether the foods and drinks affect permeability of intestinal mucosa of the test subject.

In the case of LGS, it can be determined whether LGS is induced or LGS is inhibited. The evaluation drug may be orally ingested before the eating and drinking, during the eating and drinking, or after the eating and drinking as appropriate in accordance with, for example, the kind of the food and drink.

Through the use of the evaluation drug, not only screening of a general inducer or inhibitor can be performed, but also screening of an inducer or inhibitor for an individual can be performed. That is, a risk factor for an individual can be identified.

For example, a test subject is allowed to first take the evaluation drug, and then eat meat while drinking beer. Concurrently, blood is collected every 10 minutes, and thereby, a temporal transition of LGS can be monitored. As a result, when that combination of food and drink causes the onset of medium-degree LGS in about 20 minutes for that person, the person can be advised to avoid such combination.

Further, through the use of the food and drink evaluation drug, there can be provided, for example, an objective performance index for a food touted as a conditioner for gut flora or an intestinal environment, i.e., a probiotic food. Moreover, a prebiotic food can also be evaluated.

A diagnostic device having applied thereto the technology described above can also be constructed.

That is, a diagnostic device can be obtained by including: concentration-measuring means for measuring a concentration of chitin and/or chitosan in blood collected from a test subject; and evaluation means for evaluating permeability of intestinal mucosa of the test subject on the basis of the concentration measured by the concentration-measuring means.

As a component technology of the concentration-measuring means, for example, chromatography may be used. A process from sample introduction to concentration calculation may be automated as appropriate through the use of a general technology.

The evaluation means maybe configured to, for example, determine the degree of leakiness through analysis of the position and height of a peak in an obtained chromatogram, the calculation of a peak area, and the like. Not only a mere determination as severe LGS or mild LGS, but also such a diagnosis as the following can be made on the basis of the distribution and unevenness of peaks in consideration of past data as well: being predisposed to constantly having mild LGS though not predisposed to having medium-degree LGS or severe LGS; predisposed to having medium-degree LGS by taking exercise; or having an intestinal disease other than LGS.

Besides, a specific detection antibody maybe generated, and an ELISA kit using the antibody may be adopted. With this, a large number of samples can be evaluated at once.

The blood used for measurement and diagnosis is disposed of without being returned to a human body.

INDUSTRIAL APPLICABILITY

According to the present invention, an objective index and diagnosis system for LGS can be constructed. In addition, involvement of LGS in various diseases can be explored. For example, its relationship with chronic renal disorder, bronchitic asthma, type I diabetes, food allergy, alcoholic hepatitis, nonalcoholic steatohepatitis, or the like can be investigated. A contribution can also be made to the development of a therapeutic drug for an intestinal disease.

The invention claimed is:

1. A diagnostic method, comprising:
orally administering or enema administering chitin and/or chitosan that is not labeled with FITC to an animal, the animal being other than a human;
measuring a concentration of the chitin and/or chitosan in blood of the animal to which the chitin and/or chitosan are orally administered or enema administered, after a lapse of a predetermined period of time; and
evaluating permeability of intestinal mucosa of the animal based on the measured concentration of the chitin and/or chitosan in the blood as compared to a concentration of chitin and/or chitosan in blood of a control having an intestinal tract in a normal state, to which the chitin and/or chitosan are orally administered or enema administered.

2. A diagnostic method, comprising:
orally administering or enema administering chitin and/or chitosan that is not labeled with FITC to a test subject;
measuring a concentration of the chitin and/or chitosan in blood of the test subject to which the chitin and/or chitosan are orally administered or enema administered, after a lapse of a predetermined period of time; and
evaluating a degree of leaky gut syndrome of the test subject based on the measured concentration of the chitin and/or chitosan in the blood as compared to a concentration of chitin and/or chitosan in blood of a control which does not have leaky gut syndrome and to which the chitin and/or chitosan are orally administered or enema administered.

3. A diagnostic method according to claim 1 or 2, wherein the chitin and/or chitosan has a weight average molecular weight prepared to a range of from 1,000 to 11,600.

4. A diagnostic method according to claim 1, wherein the concentration of the chitin and/or chitosan in blood is measured by:
extracting plasma from the blood;
decomposing chitin and/or chitosan in the extracted plasma into chitose;
reacting an aldehyde group of the chitose with 3-methyl-2-benzothiazolinone hydrazone hydrochloride and iron (III) chloride to develop a blue color;
measuring a degree of the blue color with an absorbance meter; and
calculating the concentration of the chitin and/or chitosan in blood on the basis of the measured degree of the blue color.

5. A diagnostic method according to claim 2, wherein a dose of the chitin and/or chitosan is set to a range of from 8.33 mg to 20.83 mg per kg of body weight.

6. A diagnostic method according to claim 2, wherein the concentration of the chitin and/or chitosan in blood is measured by:
extracting plasma from the blood;
decomposing chitin and/or chitosan in the extracted plasma into chitose;
reacting an aldehyde group of the chitose with 3-methyl-2-benzothiazolinone hydrazone hydrochloride and iron (III) chloride to develop a blue color;
measuring a degree of the blue color with an absorbance meter; and
calculating the concentration of the chitin and/or chitosan in blood on the basis of the measured degree of the blue color.

7. A food and drink evaluation method, comprising:
allowing a test subject to eat and drink a single or a plurality of specific foods and drinks;
allowing the test subject to orally ingest chitin and/or chitosan that is not labeled with FITC during the eating and drinking, or before or after the eating and drinking;
measuring a first concentration of the chitin and/or chitosan in blood of the test subject collected after a lapse of a first predetermined period of time from the oral ingestion;
measuring a second concentration of the chitin and/or chitosan in blood of the test subject collected after a lapse of a second predetermined period of time from the oral ingestion, the second predetermined period of time is later than the first predetermined period of time; and
determining whether the single or plurality of specific foods and drinks have a potential to serve as a factor increasing or decreasing permeability of intestinal mucosa of the test subject based on the measured first concentration of the chitin and/or chitosan in the blood and the measured second concentration of the chitin and/or chitosan in the blood.

8. A food and drink evaluation method according to claim 7, wherein the concentration of the chitin and/or chitosan in blood is measured by:
extracting plasma from the blood;
decomposing chitin and/or chitosan in the extracted plasma into chitose;
reacting an aldehyde group of the chitose with 3-methyl-2-benzothiazolinone hydrazone hydrochloride and iron (III) chloride to develop a blue color;
measuring a degree of the blue color with an absorbance meter; and
calculating the concentration of the chitin and/or chitosan in blood on the basis of the measured degree of the blue color.

9. An evaluation method, comprising:
administering a given substance to a test subject;
separately orally administering or enema administering chitin and/or chitosan that is not labeled with FITC to the test subject;
measuring blood concentrations of the chitin and/or chitosan in blood of the test subject before and after the administration of the given substance; and
evaluating whether the given substance has a normalizing action on permeability of intestinal mucosa, and how strong the normalizing action, when present, is, based on the measured concentration of the chitin and/or chitosan in the blood of the test subject after the administration of the given substance as compared to the measured concentration of the chitin and/or chitosan in the blood of the test subject before the administration of the given substance.

10. An evaluation method according to claim 9, wherein the concentration of the chitin and/or chitosan in blood is measured by:
extracting plasma from the blood;
decomposing chitin and/or chitosan in the extracted plasma into chitose;
reacting an aldehyde group of the chitose with 3-methyl-2-benzothiazolinone hydrazone hydrochloride and iron (III) chloride to develop a blue color;
measuring a degree of the blue color with an absorbance meter; and calculating the concentration of the chitin and/or chitosan in blood on the basis of the measured degree of the blue color.

\* \* \* \* \*